United States Patent
Engelbart et al.

(10) Patent No.: US 8,184,281 B2
(45) Date of Patent: May 22, 2012

(54) METHODS FOR DETERMINING INCONSISTENCY CHARACTERISTICS OF A COMPOSITE STRUCTURE

(75) Inventors: Roger W. Engelbart, St. Louis, MO (US); Reed Hannebaum, Mount Vernon, IL (US); Steve Schrader, Bridgeton, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 12/813,329

(22) Filed: Jun. 10, 2010

(65) Prior Publication Data

US 2010/0303335 A1 Dec. 2, 2010

Related U.S. Application Data

(62) Division of application No. 11/832,853, filed on Aug. 2, 2007, now Pat. No. 7,769,224, which is a division of application No. 10/726,099, filed on Dec. 2, 2003, now Pat. No. 7,289,656.

(51) Int. Cl.
*G01N 21/00* (2006.01)
(52) U.S. Cl. ............... 356/237.1; 356/237.4; 356/237.5
(58) Field of Classification Search .......... 356/213–236, 356/445–448, 450–458
See application file for complete search history.

(56) References Cited

U.S. PATENT DOCUMENTS

| | | | |
|---|---|---|---|
| 3,879,245 A | 4/1975 | Fetherston et al. | |
| 4,064,534 A | 12/1977 | Chen et al. | |
| 4,223,346 A * | 9/1980 | Neiheisel et al. | 348/131 |
| 4,310,132 A | 1/1982 | Frosch et al. | |
| 4,507,564 A * | 3/1985 | Shimada | 250/559.48 |
| 4,548,859 A | 10/1985 | Kline et al. | |
| 4,573,183 A | 2/1986 | Relihan | |
| 4,608,220 A | 8/1986 | Caldwell et al. | |
| 4,693,678 A | 9/1987 | Von Volkli | |
| 4,699,683 A | 10/1987 | McCowin | |
| 4,760,444 A | 7/1988 | Nielson et al. | |
| 4,780,262 A | 10/1988 | VonVolkli | |
| 4,790,898 A | 12/1988 | Woods | |
| 4,830,298 A | 5/1989 | Van Blunk | |
| 4,877,471 A | 10/1989 | McCowin et al. | |

(Continued)

FOREIGN PATENT DOCUMENTS

EP 0319797 A2 6/1989

(Continued)

OTHER PUBLICATIONS

USPTO Notice of Allowance for U.S. Appl. No. 10/726,099 dated Jun. 18, 2007.

(Continued)

*Primary Examiner* — Gregory J Toatley
*Assistant Examiner* — Jarreas C Underwood
(74) *Attorney, Agent, or Firm* — Yee & Associates, P.C.

(57) ABSTRACT

Methods for determining an inconsistency characteristic of a composite structure, such as inconsistency density-per-unit area. In one implementation, a method is disclosed for determining an inconsistency characteristic of a composite structure. The method involves determining a first distance from a first reference point of the composite structure to an inconsistency; determining a second distance from a second reference point of the composite structure to the inconsistency; using the first and second distances to establish a reference area of the composite structure; and considering each inconsistency detected within the reference area and producing therefrom an inconsistency characteristic representative of the composite structure.

10 Claims, 14 Drawing Sheets

U.S. PATENT DOCUMENTS

| | | |
|---|---|---|
| 4,941,182 A | 7/1990 | Patel |
| 4,973,838 A | 11/1990 | Bell et al. |
| 4,986,189 A | 1/1991 | Theurer et al. |
| 5,024,399 A | 6/1991 | Barquet et al. |
| 5,058,497 A | 10/1991 | Bishop et al. |
| 5,153,668 A | 10/1992 | Katzir et al. |
| 5,198,983 A | 3/1993 | Blake et al. |
| 5,337,647 A | 8/1994 | Roberts et al. |
| 5,401,115 A | 3/1995 | Musil et al. |
| 5,412,302 A | 5/1995 | Kido et al. |
| 5,439,549 A | 8/1995 | Fryc et al. |
| 5,450,147 A | 9/1995 | Dorsey-Palmateer |
| 5,518,208 A | 5/1996 | Roseburg |
| 5,540,126 A | 7/1996 | Piramoon |
| 5,562,788 A | 10/1996 | Kitson et al. |
| 5,651,600 A | 7/1997 | Dorsey-Palmateer |
| 5,683,646 A | 11/1997 | Reiling, Jr. |
| 5,689,340 A | 11/1997 | Young |
| 5,700,337 A | 12/1997 | Jacobs et al. |
| 5,746,553 A | 5/1998 | Engwall |
| 5,804,276 A | 9/1998 | Jacobs et al. |
| 5,814,386 A | 9/1998 | Vasiliev et al. |
| 5,822,055 A | 10/1998 | Tsai et al. |
| 5,825,495 A | 10/1998 | Huber |
| 5,866,820 A | 2/1999 | Camplin et al. |
| 5,871,117 A | 2/1999 | Protasov et al. |
| 5,917,588 A | 6/1999 | Addiego |
| 5,949,901 A | 9/1999 | Nichani et al. |
| 5,963,660 A | 10/1999 | Koontz et al. |
| 5,979,531 A | 11/1999 | Barr et al. |
| 6,012,883 A | 1/2000 | Engwall et al. |
| 6,013,341 A | 1/2000 | Medvedev et al. |
| 6,045,651 A | 4/2000 | Kline et al. |
| 6,064,429 A | 5/2000 | Belk et al. |
| 6,074,716 A | 6/2000 | Tsotsis |
| 6,075,883 A | 6/2000 | Stern et al. |
| 6,086,696 A | 7/2000 | Gallagher |
| 6,106,649 A | 8/2000 | Slyne et al. |
| 6,112,792 A | 9/2000 | Barr et al. |
| 6,168,358 B1 | 1/2001 | Engwall et al. |
| 6,184,924 B1 | 2/2001 | Schneider et al. |
| 6,205,239 B1 | 3/2001 | Lin et al. |
| 6,277,230 B1* | 8/2001 | Milko .......................... 156/230 |
| 6,364,250 B1 | 4/2002 | Brinck et al. |
| 6,369,492 B1 | 4/2002 | Sugimoto et al. |
| 6,390,169 B1 | 5/2002 | Johnson |
| 6,451,152 B1 | 9/2002 | Holmes et al. |
| 6,480,271 B1 | 11/2002 | Cloud et al. |
| 6,547,769 B2 | 4/2003 | VanTassel et al. |
| 6,569,513 B2 | 5/2003 | Yamaji et al. |
| 6,639,662 B2 | 10/2003 | Vaez-Iravani et al. |
| 6,648,273 B2 | 11/2003 | Anast |
| 6,692,681 B1 | 2/2004 | Lunde |
| 6,725,123 B1 | 4/2004 | Denuell et al. |
| 6,799,619 B2 | 10/2004 | Holmes et al. |
| 6,814,822 B2 | 11/2004 | Holmes et al. |
| 6,871,684 B2 | 3/2005 | Engelbart et al. |
| 6,937,753 B1 | 8/2005 | O'Dell et al. |
| 7,039,348 B2 | 5/2006 | Kerxhalli et al. |
| 7,039,485 B2 | 5/2006 | Engelbart et al. |
| 7,048,024 B2 | 5/2006 | Clark et al. |
| 7,080,441 B2 | 7/2006 | Braun et al. |
| 7,083,698 B2 | 8/2006 | Engwall et al. |
| 7,134,629 B2 | 11/2006 | Johnson et al. |
| 7,137,182 B2 | 11/2006 | Nelson |
| 7,159,822 B2 | 1/2007 | Grantham et al. |
| 7,171,033 B2 | 1/2007 | Engelbart et al. |
| 7,190,459 B2 | 3/2007 | Reinhorn |
| 7,193,696 B2 | 3/2007 | Engelbart et al. |
| 7,197,177 B2 | 3/2007 | Lowe |
| 7,228,611 B2 | 6/2007 | Anderson et al. |
| 7,236,625 B2 | 6/2007 | Engelbart et al. |
| 7,282,107 B2 | 10/2007 | Johnson et al. |
| 7,289,656 B2 | 10/2007 | Engelbart et al. |
| 7,325,771 B2 | 2/2008 | Stulc et al. |
| 7,350,379 B2 | 4/2008 | Ueda et al. |
| 7,362,437 B2 | 4/2008 | Engelbart et al. |
| 7,372,556 B2 | 5/2008 | Engelbart et al. |
| 7,424,902 B2 | 9/2008 | Engelbart et al. |
| 7,435,947 B2 | 10/2008 | Engelbart et al. |
| 7,513,964 B2 | 4/2009 | Ritter et al. |
| 7,527,222 B2 | 5/2009 | Biornstad et al. |
| 7,716,835 B2 | 5/2010 | Johnson et al. |
| 7,769,224 B2 | 8/2010 | Engelbart et al. |
| 7,835,567 B2 | 11/2010 | Oldani |
| 7,889,907 B2 | 2/2011 | Engelbart et al. |
| 2001/0002149 A1 | 5/2001 | Vaez-Iravani et al. |
| 2002/0176617 A1* | 11/2002 | Simonetti ..................... 382/141 |
| 2003/0230178 A1 | 12/2003 | Steadman |
| 2006/0108048 A1 | 5/2006 | Engelbart et al. |
| 2007/0034313 A1 | 2/2007 | Engelbart et al. |
| 2008/0008380 A1 | 1/2008 | Engelbart et al. |
| 2008/0246175 A1 | 10/2008 | Biornstad et al. |
| 2009/0148030 A1 | 6/2009 | Engelbart et al. |
| 2011/0073708 A1 | 3/2011 | Biornstad et al. |

FOREIGN PATENT DOCUMENTS

| | | |
|---|---|---|
| EP | 0833146 A2 | 4/1998 |
| EP | 0903574 A2 | 3/1999 |
| EP | 1030172 A2 | 8/2000 |
| EP | 1083076 A2 | 3/2001 |
| JP | 2001012930 | 1/2001 |
| JP | 04076900.2 | 5/2001 |
| WO | 9418643 A1 | 8/1994 |
| WO | 2004025385 A1 | 3/2004 |
| WO | 2006001859 A1 | 1/2006 |
| WO | 2006001860 A2 | 5/2006 |
| WO | 2007078408 A2 | 12/2007 |

OTHER PUBLICATIONS

USPTO Office Action for U.S. Appl. No. 11/832,853 dated Jun. 10, 2009.

USPTO Final Office Action for U.S. Appl. No. 11/832,853 dated Nov. 18, 2009.

USPTO Notice of Allowance for U.S. Appl. No. 11/832,853 dated Mar. 22, 2010.

Grimshaw, et al., "Advanced Technology Tape Laying for Affordable Manufacturing of Large Composite Structures", 11 pages. http://www.cinmach.com/tech/pdf/TapeLayingGrimshaw.pdf.

Evans, "Fiber Placement", Cincinnati Machine, 3 pages. http://www.cinmach.com/tech/pdf/asm.sub.—chapter.sub.—fp.pdf.

Grimshaw, "Automated Tape Laying", Cincinnati Machines, 6 pages. http://www.cinmach.com/tech/pdf/Grimshaw%20ASM%20Handbook.pdf.

Raytheon Aircraft's Hawker Horizon Reaches Fuselage Milestone, Raytheon News Release, 2 pages. http://www.beechcraft.de/Presse/2000/100900b.htm.

Fiedler, et al., "Tango Composite Fuselage Platform", SAMPE Journal, vol. 39, No. 1, Jan./Feb. 2003, pp. 57-63.

BAe 146, Flight International, May 2, 1981, 2 pages.

A Barrelful of Experience, Intervia, May 1992, 2 pages.

Raytheon, Mar. 2000, vol. 4, No. 2, 2 pages. http://www.cts.com/king/vasci/newsletter/vol42.html.

Business Aviation, Jun. 7, 2002, 1 page. http://www.aviationnow.com/avnow/news/channel.sub.—busav.jsp?view=story&- id=news/btoyo0607.xml.

Beechcraft's Composit Challenge, 2 pages. http://www.aerotalk.com/Beech.cfm.

Bruckstein, et al., "Omniview Cameras with Curved Surface Mirrors", Jun. 12, 2000, IEEE Omindirectional Vision Proceedings, 7 pages.

Premier I Features Lighter, Stronger All-Composite Fuselage, 3 pages. http://www.cinmach.com/WolfTracks4.sub.—1/MTG.sub.—WT7.htm.

http://www.cinmach.com/compnews/PressReleases/pr00-11.htm; Raytheon Aircraft Orders Four More Fiber Cincinnati Fiber Placement Systems for Industry's First Composite-Fuselage Business Jets, 2 pages.

http://www.rockymountaincomposites.com/wind.sub.—sys.htm; Filament Winding, 1 page.

U.S. Appl. No. 10/628,691, filed Jul. 28, 2003, Engelbart et al.

USPTO Office Action for U.S. Appl. No. 11/832,831 dated Apr. 15, 2009.
USPTO Final Office Action for U.S. Appl. No. 11/832,831 dated Sep. 17, 2009.
USPTO Office Action for U.S. Appl. No. 11/832,831 dated Dec. 28, 2009.
USPTO Final Office Action for U.S. Appl. No. 11/832,831 dated May 3, 2010.
USPTO Office Action for U.S. Appl. No. 11/832,831 dated Sep. 15, 2010.
USPTO Notice of Allowance for U.S. Appl. No. 11/832,831 dated Mar. 17, 2011.
EP Search Report for application No. 08253449.6 dated Feb. 13, 2009.
USPTO Office Action for U.S. Appl. No. 11/927,115 dated Feb. 22, 2011.
Sharp et al., "Material Selection/Fabrication Issues for Thermoplastic Fiber Placement", Journal of Thermoplastic Composite Materials, vol. 8, Jan. 1995, pp. 2-14.
Krupka et al., "Industrial applications of shearography for inspection of aircraft components", Proceedings of the 8th European Conference of Nondestructive Testing, Barcelona (Spain), Jun. 17-21, 2002, 'Online! Jun. 30, 2002, XP002351899 NDT.NET—Feb. 2003, vol. 8, No. 2, Retrieved Oct. 31, 2005. http://www.ndt.net/article/ecndt02/484/484.htm>.
Zhang, "Angewandte Sensorik" Ch. 4, Sensoren in Der Robotik, Nov. 11, 2003, pp. 76-113, XP002327793, retrieved Apr. 2004, p. 89. http://tech-www.infomatik.uni-hamburg.de/lehre/ws2003/vorlesungen/ang- ewandte.sub.--sensorik/vorlessung.sub.--03.pdf>.
Premier I Features Lighter, Stronger All-Composite Fuselage, 3 pages. http://www.cinmach.com/WolfTracks4.sub.--1/MTG.sub.--WT7.htm, 1998.
http://www.cinmach.com/compnews/PressReleases/pr00-11.htm; Raytheon Aircraft Orders Four More Fiber Cincinnati Fiber Placement Systems for Industry's First Composite-Fuselage Business Jets, 2 pages, Jul. 20, 2000.
http://www.rockymountaincomposites.com/wind.sub.--sys.htm; Filament Winding, 1 page, Apr. 1, 2004.
Zhang, "Angewandte Sensorik" Ch. 4, Sensoren in Der Robotik, Nov. 11, 2003, pp. 76-113, XP002327793, retrieved Apr. 2004, p. 89. http://tech-www.infomatik.uni-hamburg.de/lehre/ws2003/vorlesungen/ang- ewandte.sub.--sensorik/vorlessung. sub.--03.pdf>.

* cited by examiner

METHODS FOR DETERMINING INCONSISTENCY CHARACTERISTICS OF A COMPOSITE STRUCTURE

This application is a divisional of application Ser. No. 11/832,853, filed Aug. 2, 2007, now U.S. Pat. No. 7,769,224, which is a divisional of application Ser. No. 10/726,099, filed Dec. 2, 2003, now U.S. Pat. No. 7,289,656. The disclosures of the above applications are incorporated herein by reference.

COPYRIGHT NOTICE

A portion of the disclosure of this document contains material that is subject to copyright protection. The copyright owner has no objection to the facsimile reproduction by anyone of the patent disclosure, as it appears in the U.S. Patent and Trademark Office patent files or records, but otherwise the copyright owner reserves all copyright rights whatsoever.

CROSS-REFERENCE TO RELATED APPLICATIONS

The present application is related in subject matter to U.S. patent application Ser. No. 11/832,831 filed Aug. 2, 2007 and U.S. patent application Ser. No. 11/927,115 filed Oct. 29, 2007. The disclosures of the above applications are incorporated herein by reference.

FIELD

The present disclosure relates generally to the fabrication of composite structures with material placement machines, and more particularly (but not exclusively) to systems and methods for determining inconsistency characteristics of a composite structure, such as inconsistency density-per-unit area and/or cumulative inconsistency width-per-unit area.

BACKGROUND

Composite structures have been known in the art for many years. Although composite structures can be formed in many different manners, one advantageous technique for forming composite structures is a fiber placement or automated collation process. According to conventional automated collation techniques, one or more ribbons of composite material (also known as composite strands or tows) are laid down on a substrate with a material placement machine. The substrate may be a tool or mandrel, but, more conventionally, is formed of one or more underlying layers of composite material that have been previously laid down and compacted.

Conventional fiber placement processes utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. To complete the part, additional strips of composite material can be applied in a side-by-side manner to form layers and can be subjected to localized heat and pressure during the consolidation process.

Unfortunately, inconsistencies can occur during the placement of the composite strips onto the underlying composite structure. Such inconsistencies can include tow gaps, overlaps, dropped tows, puckers (i.e., raised regions in a tow), and twists. In addition, there are foreign objects and debris (FOD), such as resin balls and fuzz balls, that can accumulate on a surface of the composite structure which must be detected, identified and eventually removed from the ply surface.

Composite structures fabricated by automated material placement methods typically have specific maximum allowable size requirements for each inconsistency, with these requirements being established by the production program. Production programs also typically set well-defined accept/reject criteria for maximum allowable number of (i.e., density) of inconsistencies-per-unit area and maximum allowable cumulative inconsistency width-per-unit area.

To ensure that the composite laminates fabricated by fiber placement processes satisfy the requirements pertaining to inconsistency size, the structures are typically subjected to a 100% ply-by-ply visual inspection. These inspections are traditionally performed manually during which time the fiber placement machine is stopped and the process of laying materials halted until the inspection and subsequent action to address the inconsistencies, if any, are completed. In the meantime, the fabrication process has been disadvantageously slowed by the manual inspection process and machine downtime associated therewith.

Recently, systems have been developed that are capable of detecting, measuring, and marking individual inconsistencies in the composite structure. Exemplary systems and methods capable of accurately and reliably detecting, measuring and/or marking inconsistencies in a composite structure are disclosed in U.S. patent application Ser. No. 09/819,922, filed Mar. 28, 2001, U.S. patent application Ser. No. 10/217,805, filed Aug. 13, 2002, and U.S. patent application Ser. No. 10/628,691, filed Jul. 28, 2003. The entire disclosures of U.S. patent application Ser. Nos. 09/819,922, 10/217,805, and 10/628,691 are each incorporated herein by reference as if fully set forth herein.

Although these inspection systems have worked well for their intended purposes, the inventors hereof have recognized that it would be even more beneficial to provide systems and methods that are capable of determining an inconsistency characteristic of a composite structure, such as the composite structure's inconsistency density-per-unit area and/or cumulative inconsistency width-per-unit area.

SUMMARY

Methods for determining an inconsistency characteristic of a composite structure, such as inconsistency density-per-unit area and/or cumulative inconsistency width-per-unit area. In one embodiment, a method for determining an inconsistency characteristic of a composite structure generally includes: determining a first distance from a first reference point of the composite structure to an inconsistency; determining a second distance from a second reference point of the composite structure to the inconsistency; using the first and second distances to establish a reference area of the composite structure; and considering each inconsistency detected within the reference area and producing therefrom an inconsistency-characteristic representative of the composite structure.

The features, functions, and advantages can be achieved independently in various embodiments of the present disclosures or may be combined in yet other embodiments.

BRIEF DESCRIPTION OF THE DRAWINGS

The present disclosure will become more fully understood from the detailed description and the accompanying drawings, wherein.

Corresponding reference characters indicate corresponding features throughout the several views of the drawings.

DETAILED DESCRIPTION

According to one aspect, the present disclosure provides a method for determining an inconsistency characteristic of a composite structure, such as inconsistency density-per-unit area and/or cumulative inconsistency width-per-unit area. In one embodiment, the method generally includes: determining a first distance from a first reference point of the composite structure to an inconsistency; determining a second distance from a second reference point of the composite structure to the inconsistency; using the first and second distances to establish a reference area of the composite structure; and considering each inconsistency detected within the reference area and producing therefrom an inconsistency characteristic representative of the composite structure.

Various embodiments of the present disclosure provide methods for determining for a reference area or region of a composite structure one or more of the following inconsistency characteristics: a total inconsistency count, total inconsistency width, inconsistency density-per-unit area (i.e., number of inconsistencies-per-unit area), cumulative inconsistency width-per-unit area and/or inconsistency location.

Various embodiments allow these inconsistency characteristics to be determined as the composite structure is being fabricated, thereby eliminating the need for manual inspection processes and the machine downtime associated therewith.

In one embodiment, the method generally includes determining a linear distance to an inconsistency along a course being laid by a material placement machine; determining a lateral distance to the inconsistency from a first end of the composite structure; using the linear and lateral distances to establish a reference area; totaling inconsistencies within the reference area; dividing the inconsistency total by the reference area to determine an inconsistency density-per-unit area; determining a width for each inconsistency within the reference area; totaling the widths of the inconsistencies within the reference area; and dividing the width total by the reference area to determine a cumulative inconsistency width-per-unit area.

In an exemplary embodiment, the method includes determining both inconsistency density-per-unit area and cumulative inconsistency width-per-unit area. Alternatively, other embodiments can include determining any one or combination of total inconsistency count, total inconsistency width, inconsistency density-per-unit area, cumulative inconsistency width-per-unit area and/or inconsistency locations. Further embodiments can include determining any one or combination of total inconsistency count, total inconsistency width, inconsistency density, cumulative inconsistency width and/or inconsistency locations for the entire composite structure in which case a reference area need not necessarily be established.

Figure 1:
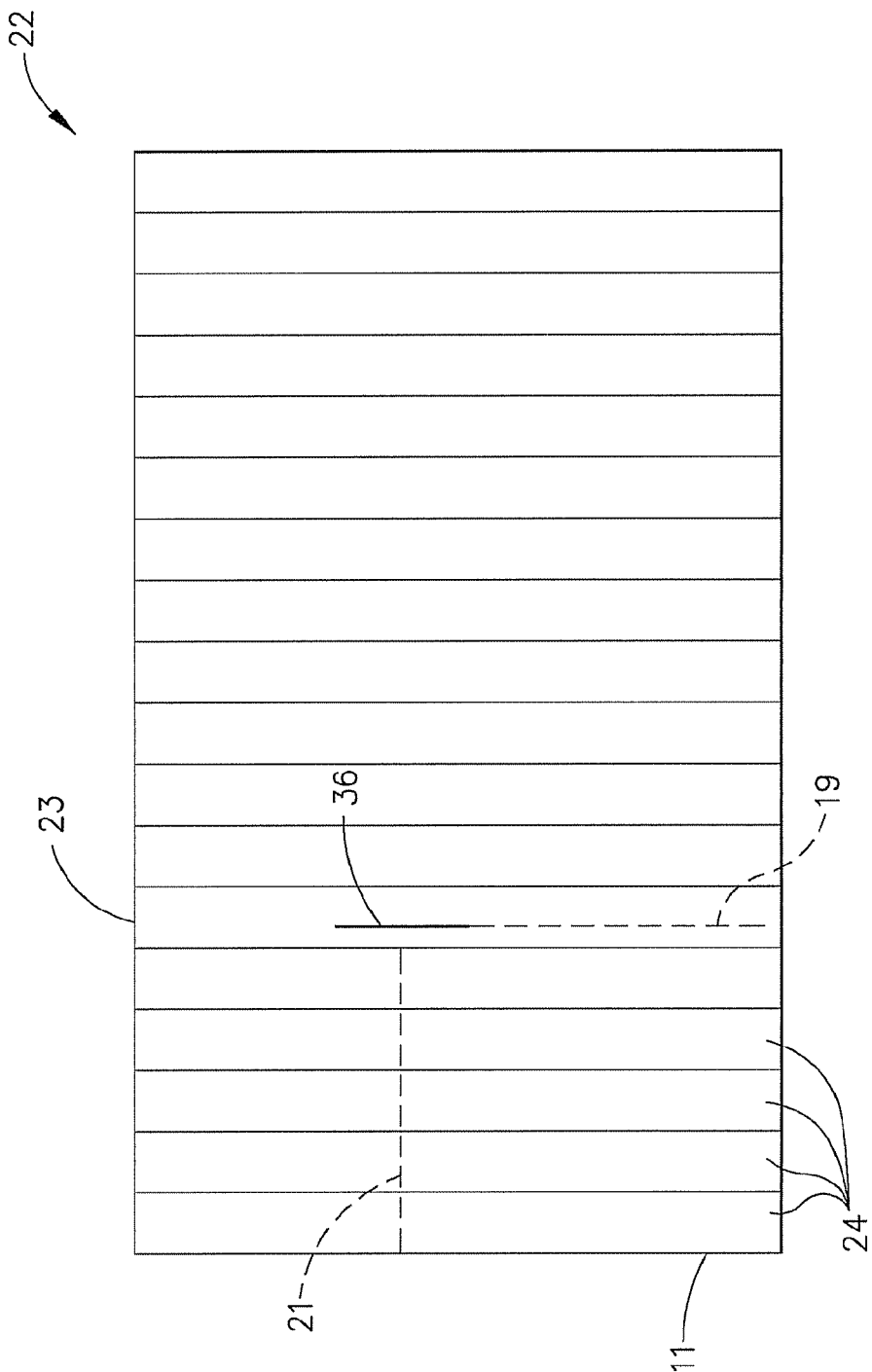
FIG. 1 is a schematic view of an exemplary composite structure illustrating linear and lateral distances to an inconsistency in the composite structure according to one embodiment of the present disclosure.

FIG. 1 illustrates an exemplary composite structure 22, which is generally comprised of a plurality of adjacent tows or strips of composite tape 24. The strips 24 typically include a plurality of fibers embedded in a resin or other material that becomes tacky or flowable upon the application of heat. The strips 24 are arranged on a work surface, such as a table, mandrel, or other tool 26 (FIG. 4), and compacted with a compaction roller 20 (FIGS. 2 and 5) to form the composite structure 22 according to an automated collation technique, such as that described in U.S. patent application Ser. No. 10/068,735, filed on Feb. 6, 2002, entitled "Composite Material Collation Machine and Associated Method for High Rate Collation of Composite Materials". The contents of U.S. patent application Ser. No. 10/068,735 is incorporated herein by reference in its entirety as if fully set forth herein.

As shown in FIG. 1, eighteen courses or strips 24 have been completed by the material placement machine. That is, the material placement machine has made eighteen passes across a substrate. During each of the passes, the material placement machine has laid down a strip 24 on the substrate.

With further reference to FIG. 1, the sixth course 23 of the composite structure 22 includes an inconsistency 36 in the form of a tow gap. Additionally, or alternatively, the composite structure 22 can also include other types of inconsistencies, such as overlaps, dropped tows, puckers, twists, and foreign objects and debris (FOD) with such inconsistencies being counted and measured by embodiments of the present disclosure.

The dashed line 19 represents the linear distance along the sixth course 23 to the inconsistency 36. The dashed line 21 represents the lateral distance to the inconsistency 36 from a first end 11 of the composite structure 22.

Various methods may be used to determine linear distances along a course to an inconsistency detected in that course. In an exemplary embodiment, linear distance to an inconsistency along a course can be determined by multiplying the linear velocity of the material placement head unit along the course with the amount of time that has lapsed between when the course began and when the inconsistency is detected.

When an inconsistency is detected, a signal can be produced that not only indicates inconsistency detection but may also trigger measurement and marking of the inconsistency. Exemplary systems and methods capable of detecting inconsistencies in a composite structure are described generally below and in more detail in U.S. patent application Ser. No. 09/819,922, filed Mar. 28, 2001, U.S. patent application Ser. No. 10/217,805, filed Aug. 13, 2002 and U.S. patent application Ser. No. 10/628,691, filed Jul. 28, 2003. The entire disclosures of U.S. patent application Ser. Nos. 09/819,922, 10/217,805, and 10/628,691 are each incorporated herein by reference as if fully set forth herein.

Figure 2:
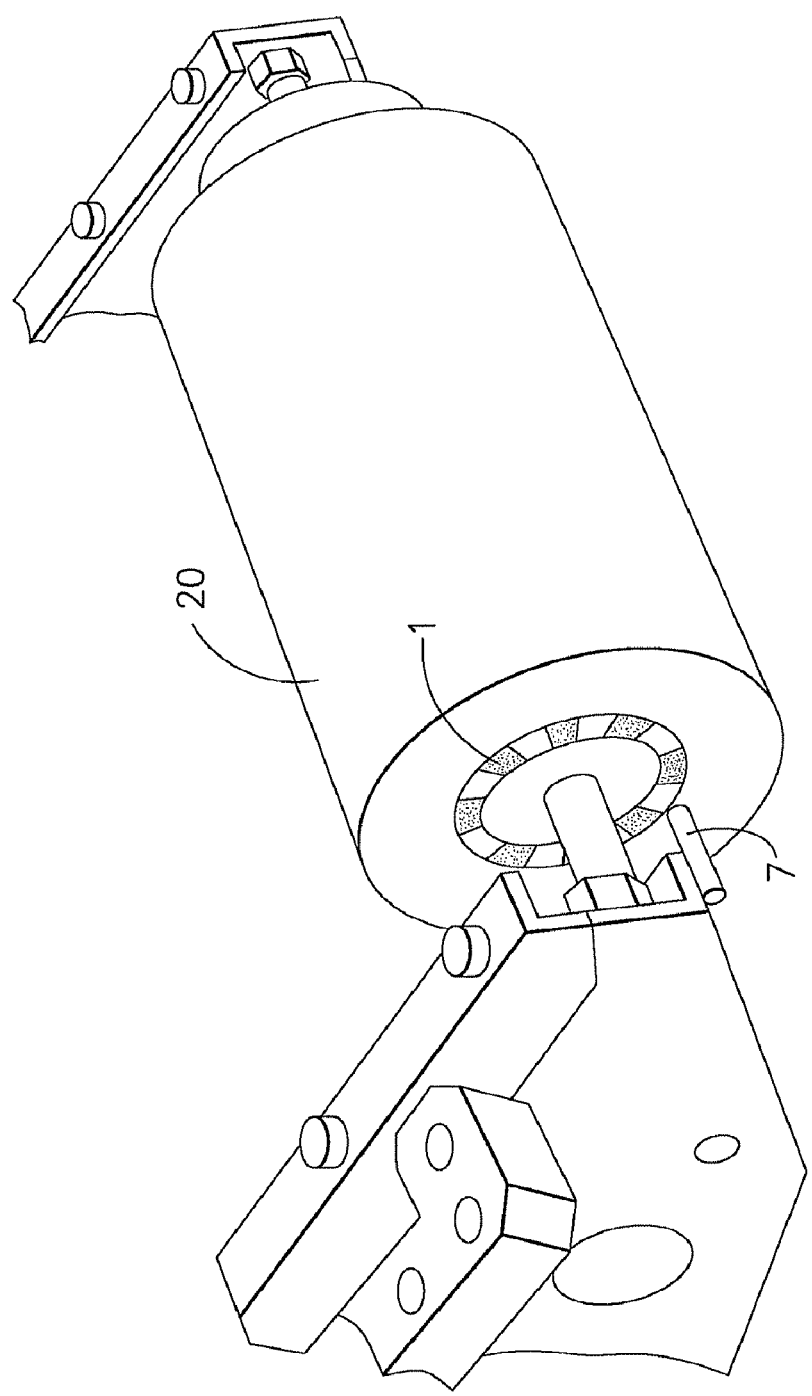
FIG. 2 is a perspective view of a compaction roller having a code ring coupled thereto for common rotation therewith and a photo sensor positioned to monitor the code ring according to one embodiment of the present disclosure.
Figure 5:
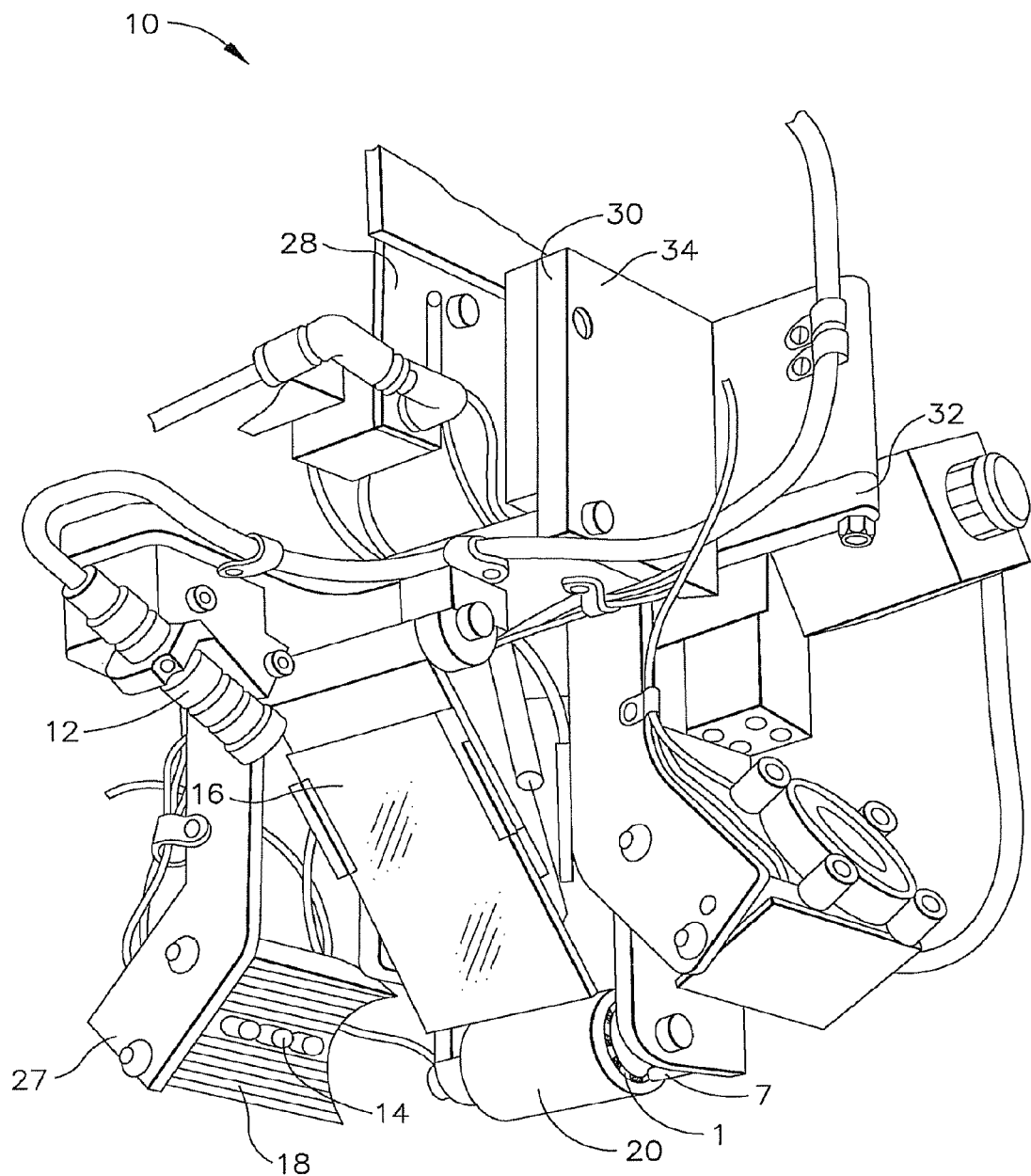
FIG. 5 is a perspective view of a system according to another embodiment of the present disclosure.

The start and stop of a course can be determined using signals from the machine load cell which indicate whether or not pressure is being applied to the compaction roller 20 (FIGS. 2 and 5). Receipt of a "pressure on" signal from the machine load cell indicates that the compaction roller 20 is in contact with the composite structure 22 and therefore, that a course has been started. Receipt of a "pressure off" signal indicates that the compaction roller 20 is no longer in contact with the composite structure 22, and therefore that a course has been completed. Accordingly, the time between course start and inconsistency detection can be determined by tracking the amount of time elapsing between receipt of the "pressure on" signal from the machine load cell and the receipt of the signal indicating detection of an inconsistency.

Alternatively, course start and stop can be determined by receipt of a signal from a device employing proximity sensors, lasers, or sound detectors positioned for determining whether or not the compaction roller 20 is in contact with the composite structure 22.

In one embodiment, the linear velocity of the head unit is determined by determining the angular velocity of the compaction roller 20 and multiplying the angular velocity by a circumference of the compaction roller 20. Alternatively, other methods can also be used to determine the linear velocity of the head unit, such as by using a radar gun commonly used for law enforcement purposes in monitoring vehicular speeds along roadways.

Figure 3:
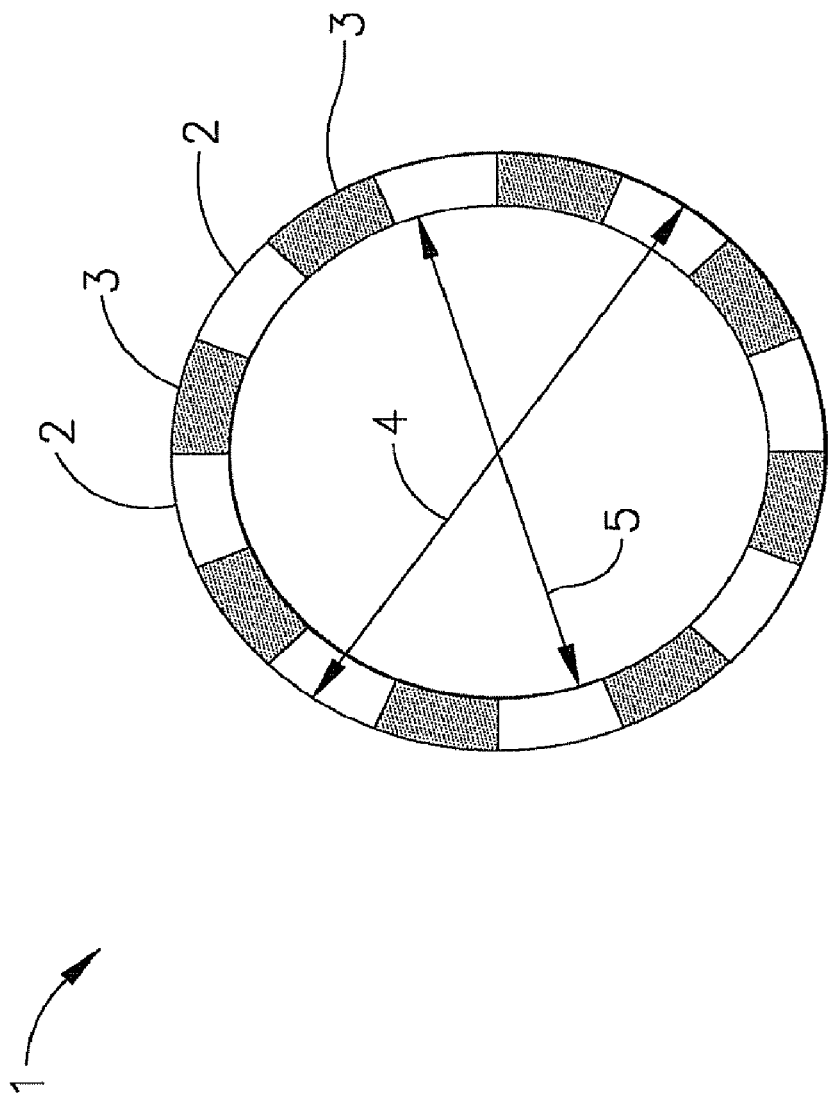
FIG. 3 is a schematic view of the code ring shown in FIG. 2.

Referring to FIGS. 2, 3 and 5, the angular velocity of the compaction roller 20 can be determined by a code ring 1 coupled for common rotation with the compaction roller 20. As shown, the code ring 1 includes alternating contrasting portions 2 and 3, such as alternating black and white segments. In FIG. 3, the code ring 1 includes an outer diameter 4 of about 1.010 inches and an inner diameter 5 of about 0.844 inches, although other ring sizes can also be employed. In other embodiments, the contrasting portions can be provided directly on the compaction roller 20 (e.g., marked on, painted on, etc.), thereby eliminating the need for the separate code ring 1.

With further reference to FIGS. 2 and 5, a photo sensor 7 (e.g., an off-the-shelf photo diode, etc.) is positioned to monitor and capture real-time images of the light-to-dark transitions of the code ring 1 as the code ring 1 rotates along with the compaction roller 20. By detecting and counting the light-to-dark transitions of the ring 1, the compaction roller revolutions can be counted and monitored. The frequency at which the light-to-dark transitions occur can be used to establish the angular velocity of the compaction roller 20. Preferably, axial motion in the compaction roller 20 is minimized in order to maintain the distance from the photo sensor 7 to the code ring 1 constant, which, in turn, allows for more accurate determination of the machine head unit's linear velocity.

In another exemplary embodiment, the linear distance to an inconsistency along a course can be determined by counting the number (whole and fractional) of revolutions the compaction roller 20 makes from the start of the course to the inconsistency and multiplying that number of revolutions by the circumference of the compaction roller 20. By way of example, the photo sensor 7 and code ring 1 can be used to count the number of revolutions of the compaction roller 20 between receipt of the "pressure on" signal from the machine load cell and receipt of the signal indicating that an inconsistency has been detected.

Various methods can also be employed to determine the lateral distances to inconsistencies from the first end 11 of the composite structure 22. See FIG. 1. In one exemplary embodiment, lateral distance to an inconsistency can be calculated by counting the total number of completed courses, not including the course in which the inconsistency resides, and then multiplying the average width of a course by the number of completed courses. This method is particularly effective for tape placement in which each course is the same width, i.e., the width of the tape.

The total number of completed courses can be determined by tracking or counting receipt of the pressure on/off signals from the machine load cell. Receipt of a "pressure on" signal from the machine load cell indicates that the compaction roller 20 is in contact with the composite structure 22 and has thus started a course. Receipt of a "pressure off" signal indicates that the compaction roller 20 is no longer in contact with the composite structure 22 and has thus completed the course.

For fiber placement courses in which the width of each course may not be equal, the lateral distances to inconsistencies can be accurately determined by employing a "software ruler." More specifically, the lateral distance can be determined by acquiring a digital image of at least the portion of the composite structure including the lateral distance; selecting a pixel set from the digital image that represents the lateral distance; counting the number of pixels comprising the pixel set; and correlating the pixel count with correlation data (e.g., a predetermined relationship between pixel count and distance) to compute an indirect quantitative measurement for the lateral distance.

The width of an inconsistency can be determined in a similar manner. After a digital image of the inconsistency has been acquired, a pixel set is selected from the digital image that represents the width of the inconsistency. The pixels comprising the pixel set are counted, and the pixel count is then correlated with correlation data (e.g., a predetermined relationship between pixel count and distance) to compute an indirect quantitative measurement for the inconsistency width.

Alternatively, inconsistency width may be determined by multiplying the linear velocity of the head unit (as determined in a manner described above) by the amount of time required for the head unit to traverse the distance separating the opposed sides of the inconsistency.

The reference area can be defined as any region of the composite structure which is currently under inspection for inconsistencies and which has a surface area about equal to the surface area of the reference area. Further, the reference area can be sized to include any suitable surface area, such as five square inches, one square foot, etc. In addition, the reference area can be sized in accordance with production requirements to include only a portion of the composite structure. Alternatively, other embodiments can utilize a reference area corresponding in size to the entire composite structure.

The reference area can be established in various ways. In one exemplary embodiment, the reference area comprises any region of the composite structure that is bounded by the linear and lateral distances to the presently detected inconsistency. For example, and referring to FIG. 1, a reference area can be established for the inconsistency 36 as the rectangular portion of the composite structure 22 defined by the dashed lines 19 and 21 and the composite structure's first end 11 and lower side edge.

In another embodiment, the reference area comprises any region of the composite structure which is bounded by a predetermined linear distance and a predetermined lateral distance.

In either of the aforementioned embodiments, the bounded reference areas can be tracked during the inspection, for example, in a lookup table. The lookup table might then be compared to a running tally of inconsistencies (e.g., running inconsistency quantity and/or running inconsistency width) during the inspection.

In yet other embodiments, the reference area is defined as the region of the composite structure which includes the preceding portion of the course in which the presently detected inconsistency resides and all of the completed, preceding courses. For example, and referring to FIG. 1, a reference area can be established for the inconsistency 36 as the first five courses to the left of course 23 and that portion of the sixth course 23 below the inconsistency 36.

In further embodiments, the reference area is defined as a region of the composite structure which includes the preceding portion of the course in which the presently detected inconsistency resides and a predetermined number of completed courses immediately preceding the course in which the presently detected inconsistency resides. For example, a reference area can be established for the inconsistency 36 as that portion of the sixth course 23 below the inconsistency 36 and the three courses (i.e., third, fourth and fifth courses) to the immediate left of the sixth course 23 in FIG. 1.

In certain embodiments, a comparison is made between the cumulative inconsistency width-per-unit area and a maximum allowable cumulative inconsistency width-per-unit area to determine whether a composite structure is acceptable or should be rejected. The maximum allowable cumulative inconsistency width-per-unit area can be set by production requirements. When the cumulative inconsistency width-per-unit area exceeds the maximum allowable cumulative inconsistency width-per-unit area, the manufacturing process can be halted and/or an indicator of unacceptability can be provided, for example, by a user interface 76 (FIG. 4) described below.

Additionally, or alternatively, certain embodiments include comparing the inconsistency density-per-unit area and a maximum allowable inconsistency density-per-unit area to determine whether a composite structure is acceptable or not. The maximum allowable inconsistency density-per-unit area can be set by the production requirements. When the inconsistency density-per-unit area exceeds the maximum allowable inconsistency density-per-unit area, the manufacturing process may be halted and/or an indicator of unacceptability may be provided, for example, via the user interface 76 (FIG. 4) described below.

Figure 4:
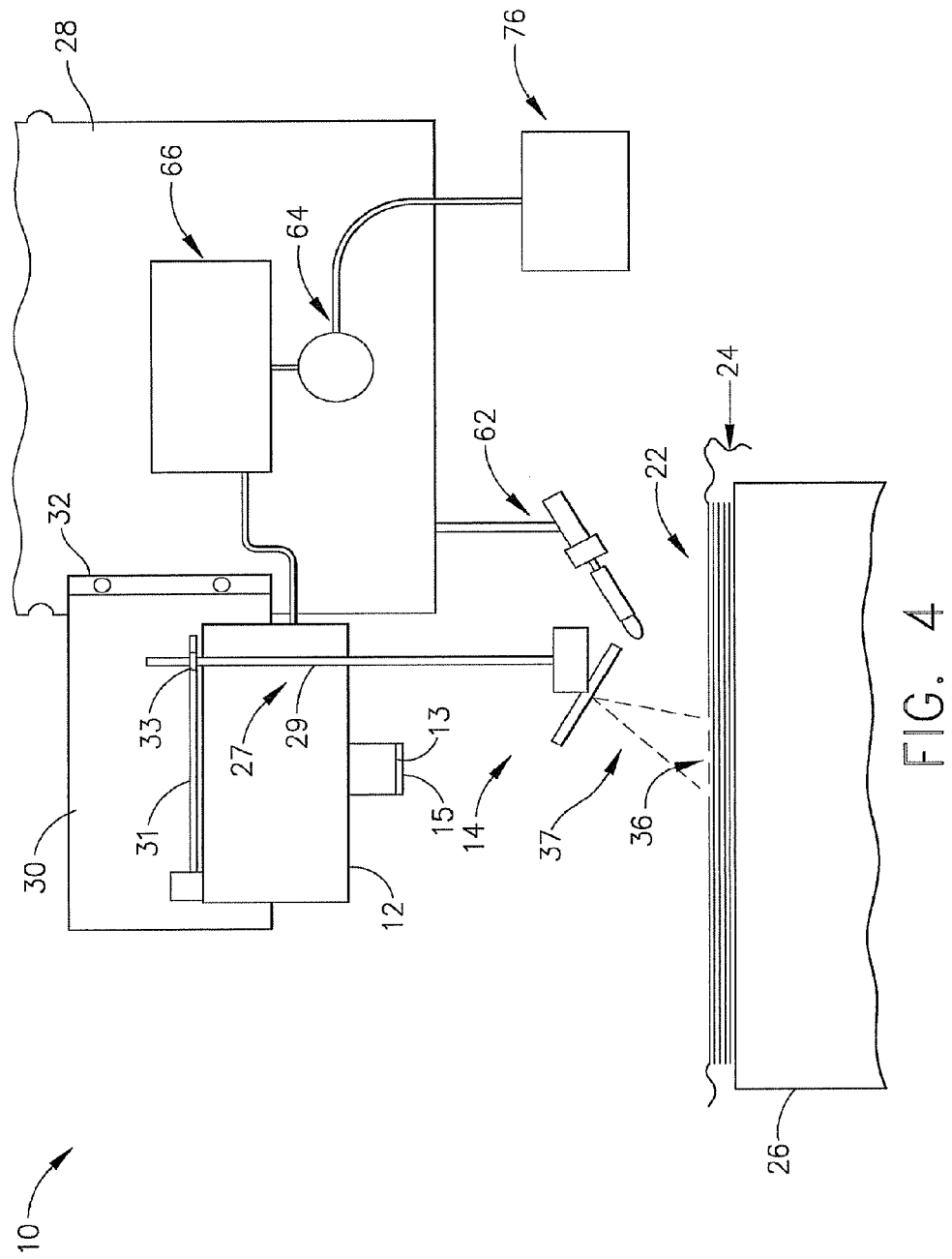
FIG. 4 is a schematic view of a system according to one embodiment of the present disclosure.

An exemplary system 10 which can be used to detect inconsistencies in a composite structure is illustrated in FIG. 4. As shown in FIG. 4, the system 10 includes at least one camera 12 and at least one light source 14. The camera 12 is connected to a processor 66 for interpreting the images the camera 12 captures, or to a storage device 64 for storing the images, or both, as discussed more fully below.

The light source 14 is positioned to emit light for illuminating the composite structure 22. The illumination is reflected differently by inconsistencies in the composite structure than from portions of the composite structure that are inconsistency free. For example, illumination reflecting off non-inconsistent portions of the composite structure 22, and light that fails to reflect off of inconsistencies in the composite structure 22, or vice versa, creates visible images that can be captured by the camera 12. Details regarding systems and methods for identifying inconsistencies in a composite structure during fabrication thereof are included in previously referred to U.S. patent application Ser. Nos. 09/819,922, 10/217,805, and 10/628,691.

As shown in FIG. 4, the camera 12 is positioned near the composite structure 22 so as to capture images of portion of the composite structure being illuminated, which is typically immediately downstream of the nip point at which a composite tow is joined with the underlying structure. Alternatively, and as shown in FIG. 5, a reflective surface 16 may be positioned near the composite structure (the composite structure is not shown in FIG. 5), and angled such that the reflective surface 16 reflects an image of the illuminated portion of the composite structure. The camera 12 may be positioned to point toward the reflective surface 16 in order to capture close-range images of the illuminated portion of the composite structure from the reflective surface 16. More than one reflective surface 16 may also be utilized in further embodiments of the present disclosure in which the reflective surfaces 16 cooperate in order to direct images of the illuminated portion of the composite structure to the camera 12.

A wide range of cameras can be used including commercially-available cameras capable of acquiring black and white images. In one embodiment, the camera 12 is a television or other type of video camera having an image sensor (not shown) and a lens 13 through which light passes when the camera 12 is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS). The camera 12 can be positioned proximate the composite structure 22 on a stand (not shown) or mounted to a frame 28 or similar device.

In those embodiments that do not include a reflective surface 16, the camera 12 may be mounted to the frame 28 by way of a bracket 30 and associated connectors 32, as shown in FIG. 4. The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the material placement device, particularly the parts located behind the camera 12 and associated assembly, must be accessed, such as for maintenance, cleaning, or the like.

FIG. 5 illustrates an alternative embodiment of the hinge-type connector 32 that mounts the camera 12, reflective surface 16, light source 14, and associated assembly (e.g., camera assembly) to the frame 28 by way of a bracket 30. A suitable fastener, such as a thumbscrew or any other fastener that may be removed or loosened with relative ease, can be inserted through hole 34 and then tightened to secure the camera assembly in place for operation. The fastener may be loosened or removed, for example, to rotate the camera assembly away from the compaction roller 20 and other parts of the fiber placement device.

With further reference to FIG. 4, a filter 15 can be placed on the lens 13 for filtering light in a particular manner. In one embodiment, the filter 15 is designed to filter light such that only the infrared component or a certain infrared wavelength or range of wavelengths of light can pass into the camera 12. In this manner, the filter 15 prevents ambient visible light from entering the camera 12 and altering the appearance of the captured image.

Other methods of filtering light can also be used to achieve the same, or at least similar, result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (e.g., an infrared-sensitive camera), thus eliminating the need for the filter.

The light source 14 of the system 10 will now be described in more detail. The light source 14 is positioned to emit light for illuminating at least a portion of the composite structure 22.

In FIG. 4, the light source 14 is shown positioned at an oblique angle 37 relative to the composite structure 22. The oblique angle 37 may be about forty-five degrees, although other angles are possible depending on the application. In addition, the light source 14 is also shown positioned to emit light in a direction substantially perpendicular to the direction of placement of the strips 24 in order to highlight the inconsistencies 36, as described below.

Figure 7:
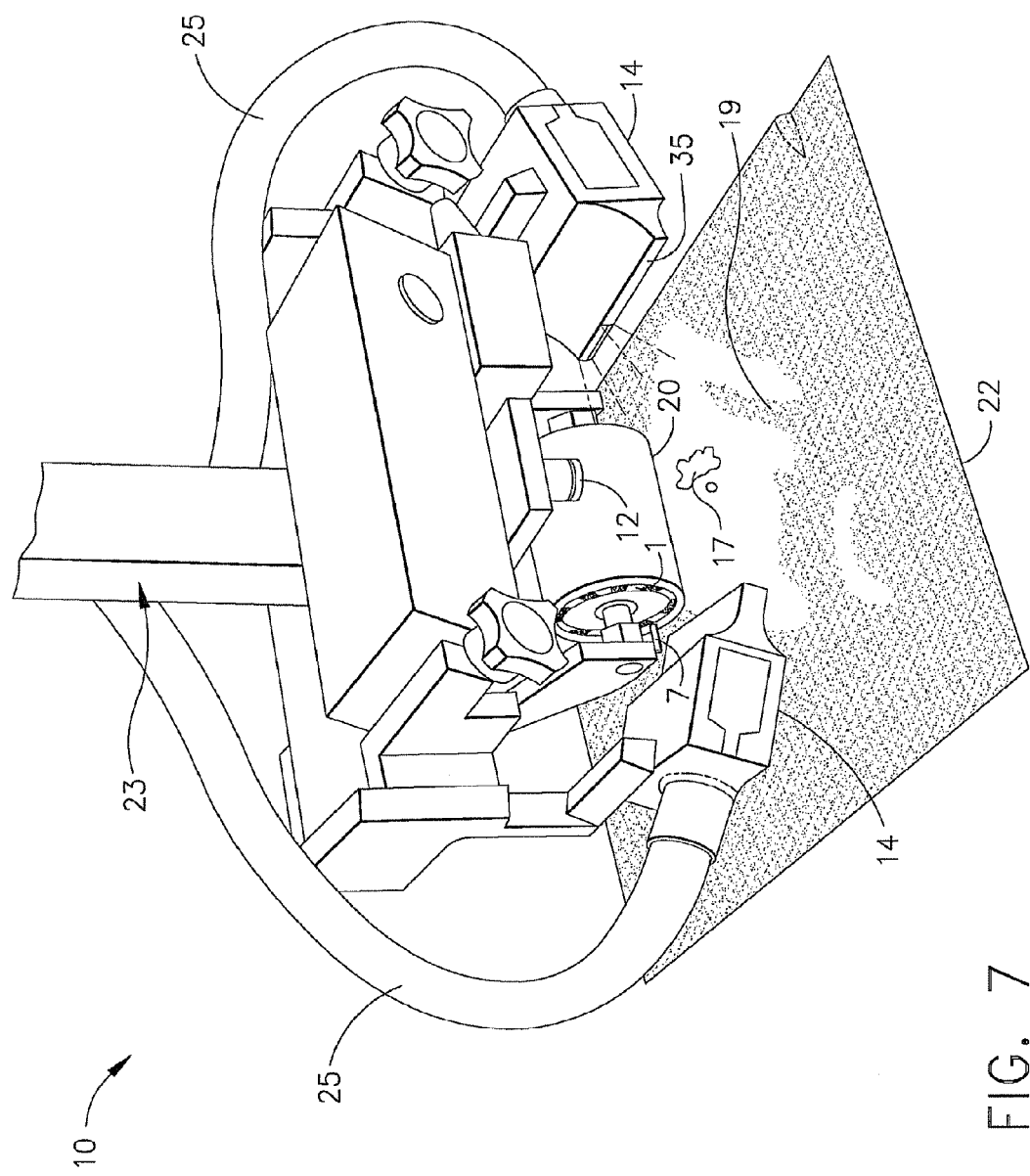
FIG. 7 is a perspective view of a system according to another embodiment of the present disclosure.

Further, the system 10 may include more than one light source. For example, the embodiment of FIG. 5 includes two light sources 14 positioned relative to the composite structure and compaction roller 20 on either side of the reflective surface 16 and camera 12. Another exemplary embodiment that includes two light sources 14 is shown in FIG. 7 in which two linear optical fiber arrays are positioned on opposed sides of the camera 12.

In FIG. 4, the light source 14 is adjustably positioned relative to the composite structure 22 by mounting or attaching the light source 14 to a mounting apparatus 27. The mounting apparatus 27 can include a main shaft 29, a secondary shaft 31, and a locking clamp 33 for quickly and accurately adjusting the position of the light source 14. The mounting apparatus 27, in turn, can be attached to the frame 28, to the camera 12, to the bracket 30, or to some other object that defines a common position for both the light source 14 and the camera 12 such that the light source 14 and camera 12 maintain a constant spatial relationship relative to one another.

The quality and magnitude of the surface illumination of the composite structure is greatly affected by ambient lighting and by the reflectivity of the material. Accordingly, embodiments of the present disclosure advantageously employ an infrared light source to more effectively illuminate dark inconsistencies on a dark background. In this regard, the light source 14 can be selected from an infrared light or another type of light having an infrared component, such as a halogen light source (FIG. 6) or other incandescent light sources (not shown). In other embodiments, the light source 14 can also include a fluorescent light source (e.g., white light LEDs, low pressure/mercury filled phosphor glass tube, etc.), a strobe or stroboscopic light source, a noble gas arc lamp (e.g., xenon arc, etc.), metal arc lamp (e.g., metal halide, etc.) and a lasers (e.g., pulsed lasers, solid state laser diode arrays, infrared diode laser arrays, etc.). The light from the light source 14 may also be pumped from optical fibers to the point of delivery, such as is shown in FIG. 7.

In some embodiments, the light source 14 is operated at a power level that maximizes, or at least significantly increases, the infrared (IR) component of the light which works well for inspecting dark tow material, such as carbon. In this regard, exemplary power levels in the range of up to about one hundred fifty watts (150 W) in the wavelength range of about seven hundred nanometers to one thousand nanometers (700 nm-1000 nm) have been sufficient. However, the particular power levels and wavelengths for the light source will likely depend at least in part on the camera's speed and sensitivity, speed at which the material is being laid, delivery losses, and reflectivity of the material being inspected, among other factors. For example, in other embodiments, wavelengths and power levels suitable for inspecting highly reflective materials can be employed.

In the embodiment shown in FIG. 4, the light source 14 may comprise a plurality of LEDs arranged in an array or cluster formation. In one specific embodiment, the light source 14 includes 24 LEDs mounted in an array upon a three-inch square printed circuit board.

Figure 6:
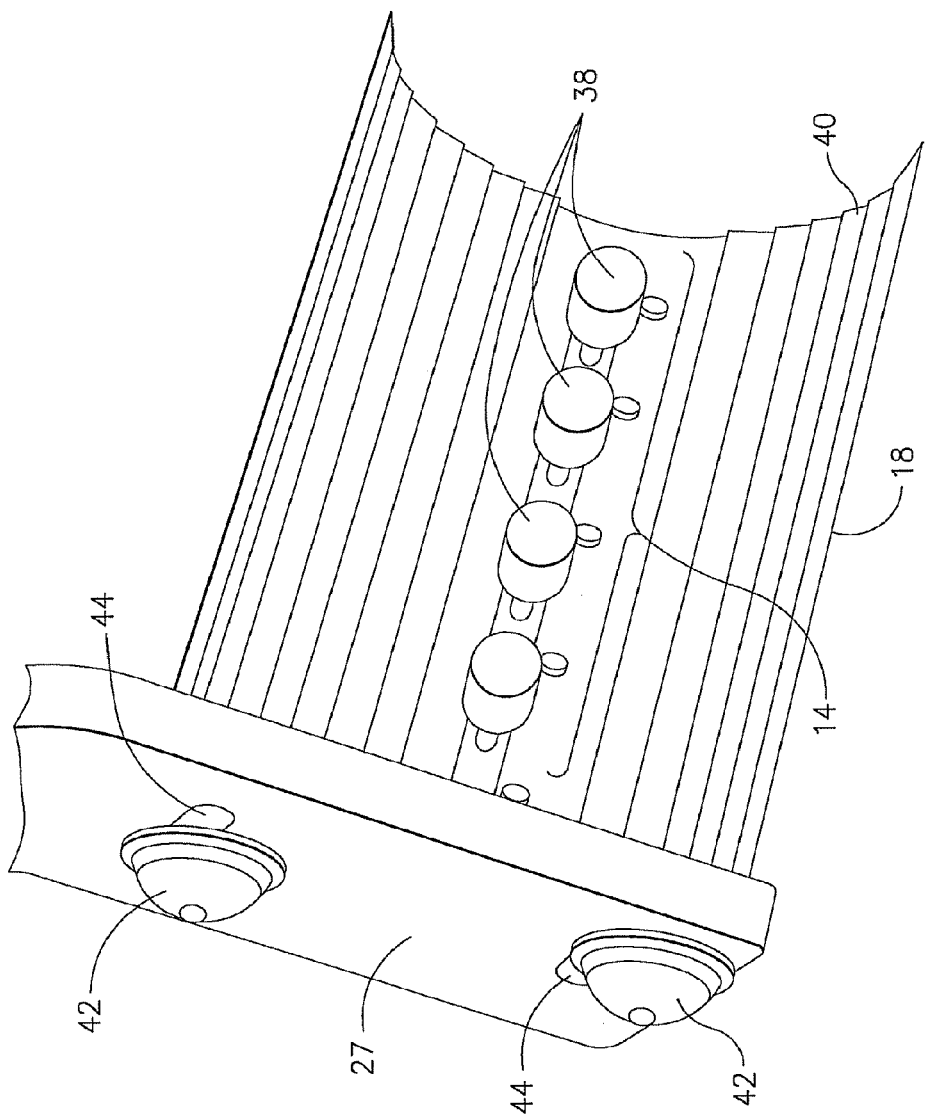
FIG. 6 is a perspective view of a light source according to the system embodiment shown in FIG. 5.

In another embodiment shown in FIGS. 5 and 6, the light source 14 includes four halogen light bulbs 38, although other quantities can also be used.

Figure 8:
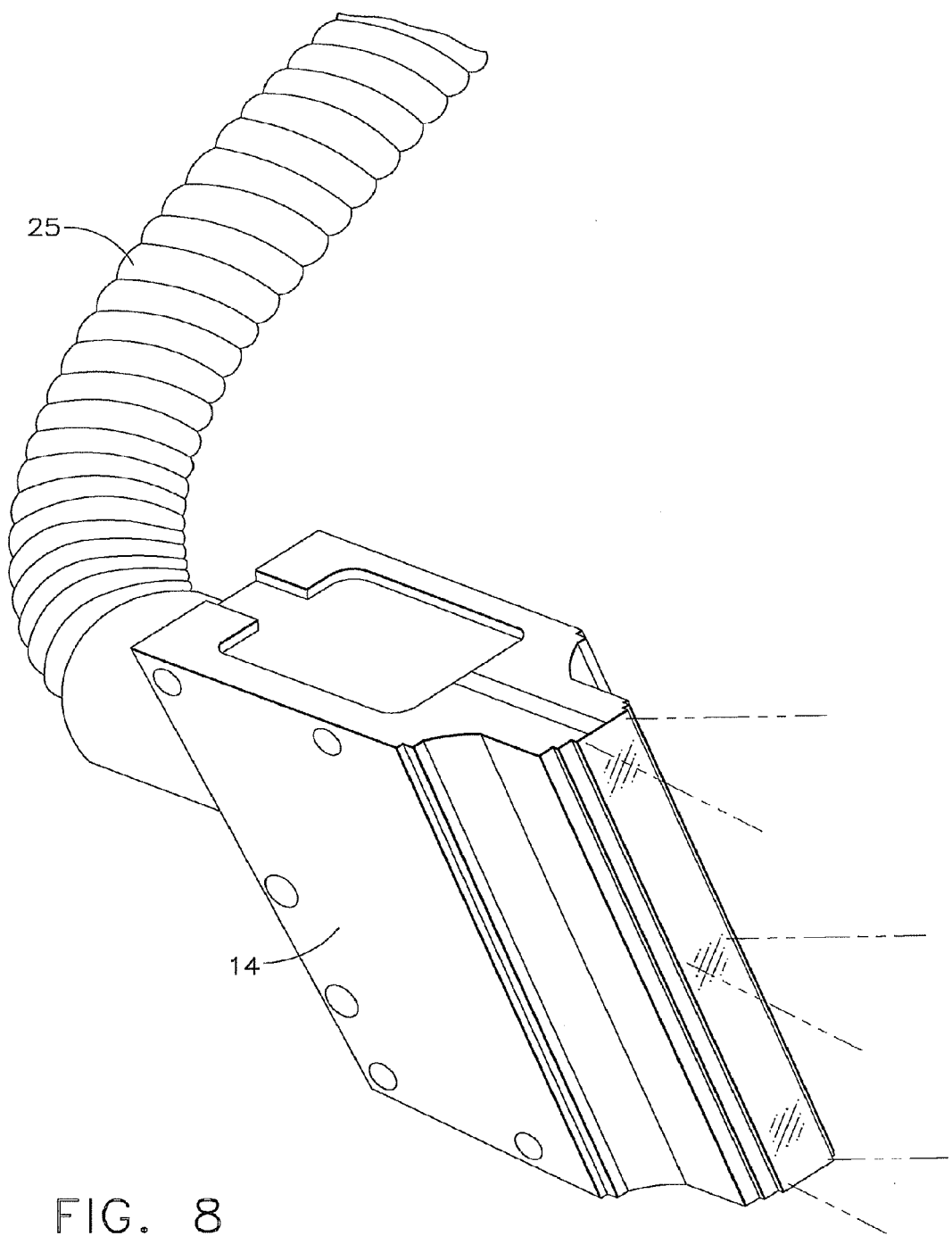
FIG. 8 is a perspective view of a light source according to the system embodiment shown in FIG. 7.

In the embodiment shown in FIG. 7, the light source 14 includes two linear optical fiber arrays positioned on opposite sides of the camera 12. The arrays emit light supplied from a remote source (not shown) through an optical fiber bundle 25. An illuminated linear array 14 is shown in FIG. 8.

Referring back to FIG. 5, the system 10 may further include a light reflection element 18 located near the light source 14. The reflection element 18 include a series of light reflecting surfaces 40 (FIG. 6) that redirect the light towards the desired area to be illuminated. This levels the illumination across the surface and eliminates, or at least substantially reduce, areas of intense light (i.e., hotspots) created by the brightest portion of the light source 14. Hotspots are undesirable because hotspots prevent consistent illumination of the composite structure, which may lead to inconsistencies during the processing of the images captured by the camera 12.

The light reflection elements 40 are particularly advantageous for illuminating curved/contoured surfaces of composite structures because the redirection of the light permits a larger portion of the composite structure to be evenly illuminated.

As shown in FIG. 6, the reflection element 18 is curved around the light source 14, such as in a parabolic shape. On the surface of the reflection element 18 that faces the light source 14, the reflection element 18 includes curved steps 40 substantially parallel to the light source 14. The distance between and curvature of the steps 40 can be chosen to be sufficient to provide even illumination from the sum of the two light sources, one on either side of the region of interest. This enables the reflection element 18 to provide more consistent illumination of the composite structure 22, which prevents, or at least reduces, image processing errors due to inconsistent illumination of the composite structure 22. Alternatively, the shape and/or surface configuration of the reflection element 18 can be modified in other ways that also produce consistent illumination and scattering of the light produced by the light source 14 over the desired portion of the composite structure 22.

In an exemplary embodiment, the reflection element 18 has an overall parabolic shape with seventeen parabolic curved steps 40 having a range of widths from about 0.125 inches at the outer edge of the reflection element 18 to about 0.250 inches at the center of the reflection element 18. The reflection element 18 also has a uniform step height of about 0.116 inches. In other embodiments, however, the reflection element may be provided with different numbers of steps having different uniform or varying widths and different uniform or varying step heights.

Furthermore, the reflection element 18 may be adjusted in order to direct the light produced by the light source 14 and scattered by the reflection element 18 toward the desired portion of the composite structure. For example, as shown in FIG. 6, the reflection element 18 is adjustably mounted to the mounting apparatus 27 with fasteners 42. The loosened fasteners 42 can move within slots 44 to correspondingly adjust the angle of the reflection element 18 relative to the composite structure. Once the reflection element 18 is positioned appropriately, the fasteners 42 are tightened to secure the reflection element 18 in the desired position. Adjustments of the reflection element 18 can also be enabled by other methods, such as by electronic means that permit remote adjustment of the reflection element 18.

It has been observed that the composite structure 22 produces high glare when illuminated across the direction of placement of the strips 24 but produces substantially less glare when illuminated along the direction of placement of the strips 24. The systems and methods of at least some embodiments exploit the high-glare/low-glare phenomenon by casting light across the top layer of the composite strips 24 in a direction substantially perpendicular to the direction of placement of the strips 24. This produces a relatively large amount of glare on the top layer of the composite structure 22. The underlying layers, which produce significantly less glare than the top layer because of their orientation, will show through any gaps or other inconsistencies in the top layer and thus be easily located. In addition, twists and other surface inconsistencies in the top layer will alter the orientation of the strips in the top layer and thus correspondingly alter, i.e., decrease, the glare of the top layer at the inconsistent location.

While the high-glare/low-glare phenomenon occurs when illuminated with either visible light or infrared light, the filter 15 used in one embodiment of the system 10 substantially removes the glare caused by ambient light such that only the glare caused by the infrared light source is used to locate the inconsistencies. Accordingly, the filter 15 removes the interference of ambient light as the composite structure 22 is being examined for inconsistencies.

In any of the system embodiments described herein, there may be one or more cameras 12 and/or one or more light sources 14 with or without reflection elements 18 (collectively referred to as light sources, hereinafter). In addition, the one or more cameras 12 and/or the one or more light sources 14 may be moveable relative to the composite structure. The multiple cameras 12 and/or multiple light sources 14 and the moveability of the camera(s) 12 and/or the light source(s) provides system 10 flexibility in order to capture the most accurate images of the composite structure. Multiple and/or moveable light source(s) 14 permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip. Systems including moveable cameras and light sources are described in detail in previously referred to U.S. patent application Ser. No. 10/217,805.

As shown in FIG. 4, the system 10 can also include a marking device 62 for marking the location of inconsistencies on the composite structure 22. The marking device 62 may be attached to the frame 28 and be triggered by a processor 66 or similar device when an inconsistency 36 is detected. The marking device 62 may spray or otherwise deposit an amount of ink, paint or the like onto the composite structure 22 in those areas where inconsistencies 36 have been detected. The markings on the composite structure 22 enables the location of the inconsistencies to be subsequently readily identified either automatically or manually.

In the particular illustrated embodiment, the marking device 62 is an inkjet marking system that sprays a small spot of compatible ink of a highly visible color onto the surface of the composite structure 22 at the inconsistency location to permit rapid access for addressing the inconsistency. Alternatively, other marking methods can also be used, such as a pump-fed felt-tip marker, spring-loaded marking pen, audio or visual alerts, and the like.

The camera 12 and/or the reflective surface 16, which along with the light source 14 and any reflection element 18, can be mounted to the head unit to allow the camera 12 to continuously capture real-time images of the composite structure 22 and the strips 24 as the head unit moves across the composite structure 22 and the composite strips 24 are laid down. If the composite structure 22 is not planar, the inspection point should preferably be as close to the nip point as possible, as described above. If the composite structure 22 is planar, the inspection point can be located further from the placement head unit. In either case, the images can be stored in a memory device 64 for future analysis and/or processed immediately by the processor 66, as discussed more fully below.

Figure 9:
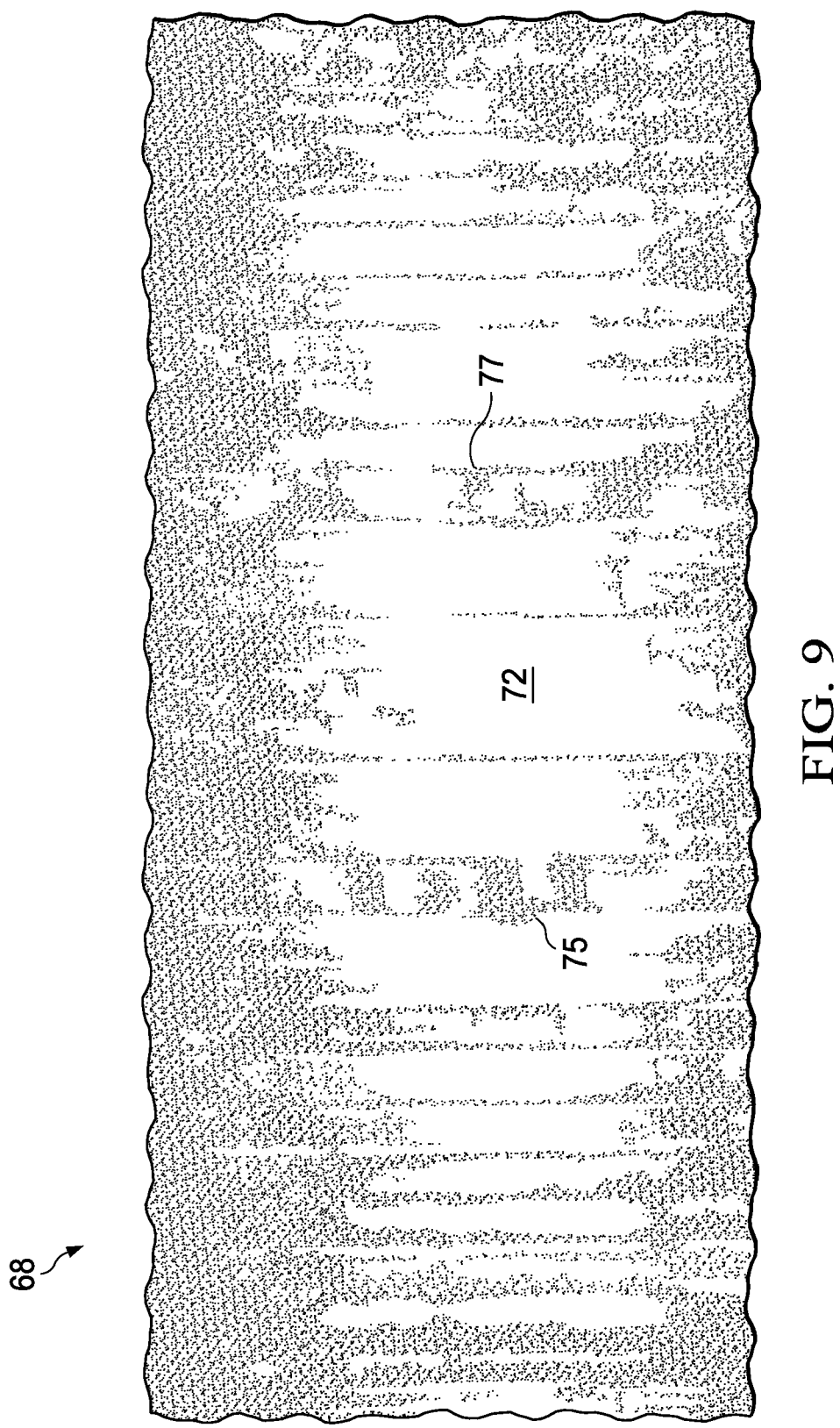
FIG. 9 is an video frame capturing a pucker and a twist in a composite structure.

FIG. 9 shows an exemplary raw or unprocessed camera image 68 illustrating a contrast between potential inconsistencies, such as a pucker 75 and a twist 77, and the remaining portions of the composite structure 22 that are inconsistency free. In the illustrated embodiment, the potential inconsistencies 75 and 77 are shown as black or gray areas, while the remaining non-inconsistent portions of the composite structure 22 remain substantially white 72. Once the potential inconsistencies are located, the inconsistencies may be marked with the marker 62 and the linear and lateral distances to the potential inconsistencies can be determined in a manner described above.

With further reference to FIG. 4, the processor 66 may receive the images 68 from the camera 12 or from the memory device 64 in which the images 68 have been stored. The processor 66 may then process and analyze the images to facilitate the reliable detection of inconsistencies. In at least one embodiment, the processor 66 and memory device 64 are components of a conventional computer.

The system 10 may also include a user interface 76 that is in communication with the processor 66. The user interface can be programmed such that it can run from a wide range of software applications, including but not limited to DOS, Windows 98, Windows/NT, Windows 2000, Windows CE, Linux, Unix, and equivalents.

Figure 10:
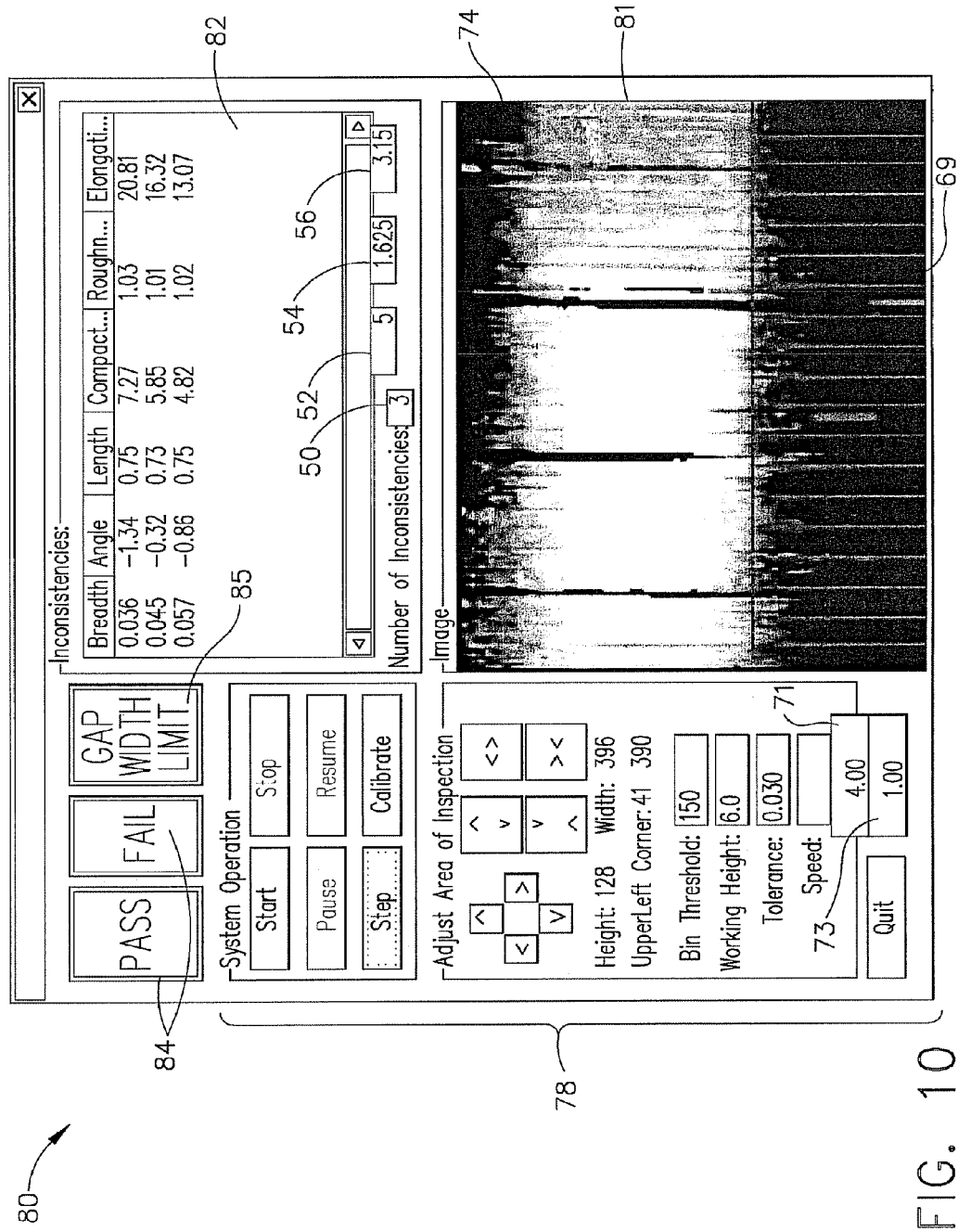
FIG. 10 is a view of a computer display and user controls according to one embodiment of the present disclosure.

As shown in FIG. 10, the user interface 76 includes a display screen 80, such as on a computer monitor, and can also include an input device, such as a keyboard and mouse (not shown), for permitting an operator to move a cursor about the display screen 80 and input various system settings and parameters. The display screen 80 can also be touch-sensitive for permitting the operator to input the desired settings by manually touching regions of the display screen.

The user interface 76 includes a window 81 in which an image 74 of the composite structure 22 is displayed for viewing by the operator or other user. The window 81 can also include a visual display 69 of inconsistency location by course.

Although the image 74 can be the unprocessed camera image 68 (FIG. 9), the image 74 shown in FIG. 10 can also be a processed image that has been binarized. During binarization, all shades of gray above a predetermined threshold value can be changed to white, while all gray shades below the threshold are changed to black to heighten the contrast of inconsistencies and improve the accuracy of inconsistency detection. In other embodiments, the binarization operation need not be performed but instead the raw image, rates of change of the light levels in the raw image, and/or color changes in the images can be used to identify the inconsistencies.

The user interface 76 also provides user controls 78 for allowing various user inputs to the system. In the particular illustrated embodiment of FIG. 10, the user interface 76 allows adjustment to the binarization threshold. Generally, the setting of the binarization threshold involves a tradeoff between the sensitivity with which inconsistencies are detected and the resolution with which the inconsistencies are depicted. In one embodiment, the binarization threshold is set to about 128 which corresponds to the mid-point on the 8-bit digitizing range of 0 to 255. However, other binarization threshold values can be employed depending at least in part on the particular application, available lighting, camera settings, among other factors.

The user controls 78 also allow the user to adjust or shift the viewing area within the window 81. During operation, the window 81 displays real-time moving video images of the illuminated portion of the composite structure 22 as the camera 12 and/or the reflective surface 18 are moved relative to the composite structure 22.

The interface 76 can also allow the user to input the width of course or tow band 71 and maximum allowable cumulative gap width 73.

In addition to displaying images of the composite structure 22, the display screen 80 also includes an inconsistency table 82 which lists the discovered inconsistencies and provides information for each inconsistency, such as location, size, and the like.

The display screen 80 can also provide information (which can be continuously updated) such as the number of inconsistencies 50, number of courses completed 52 (which may be determined by counting pressure on/off signals from the machine load cell as described above), cumulative inconsistency width 54, and length of the current inconsistency being measured 56.

The display screen 80 can further include status indicators 84 that notify the user whether a particular image area is acceptable or not acceptable based on predefined criteria, such as maximum allowable dimensional parameters and tolerances.

The display screen can also include an indicator 85 that notifies the user when the allowable cumulative inconsistency width limit has been exceeded.

An exemplary embodiment includes importing a part model from external or third party software (e.g., computer aided drafting (CAD) programs, work station-based programs such as Unigraphics (UG) or CATEA, desktop PC applications such as AutoCAD, etc.)

Figure 11:
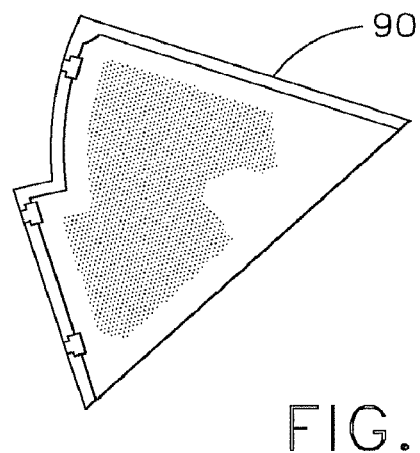
FIG. 11 is a view of an exemplary part model which may be imported from external or third party software according to one embodiment of the present disclosure.
Figure 12:
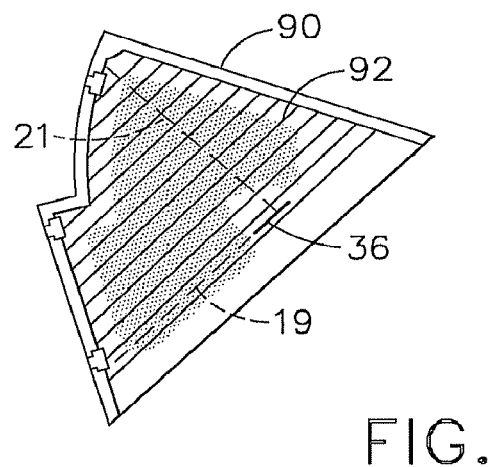
FIG. 12 is a view of the part model shown in FIG. 11 with a course grid overlay according to one embodiment of the present disclosure.

FIG. 11 illustrates an example of a complex part model 90 imported from third party software. As show in FIG. 12, a course grid overlay 92 can be constructed for the imported part model 90 using the number of courses and the direction of travel that correspond to ply orientation. The diagrammatic concepts of linear and lateral distances 19 and 21 are illustrated in FIG. 12 to show inconsistency 36 location on a surface more complex than the surface shown in FIG. 1.

Figure 13:
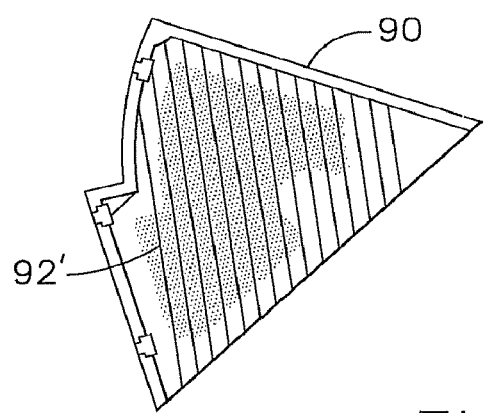
FIG. 13 is a view of the part model shown in FIG. 12 but with the course grid overlay repositioned to represent a change in orientation for the new ply according to one embodiment of the present disclosure.

After all courses for a ply have been laid, the course grid overlay 92' is repositioned to represent the change in orientation or direction of travel for the new ply, as shown in FIG. 13. The interaction between the external or third party software and the software of the material placement machine can be designed to generate an entire set of grids (one for each ply of the part) in advance. These grids can be stored, with the appropriate grid being accessed, called up and positioned at the start of each ply.

Figure 14:
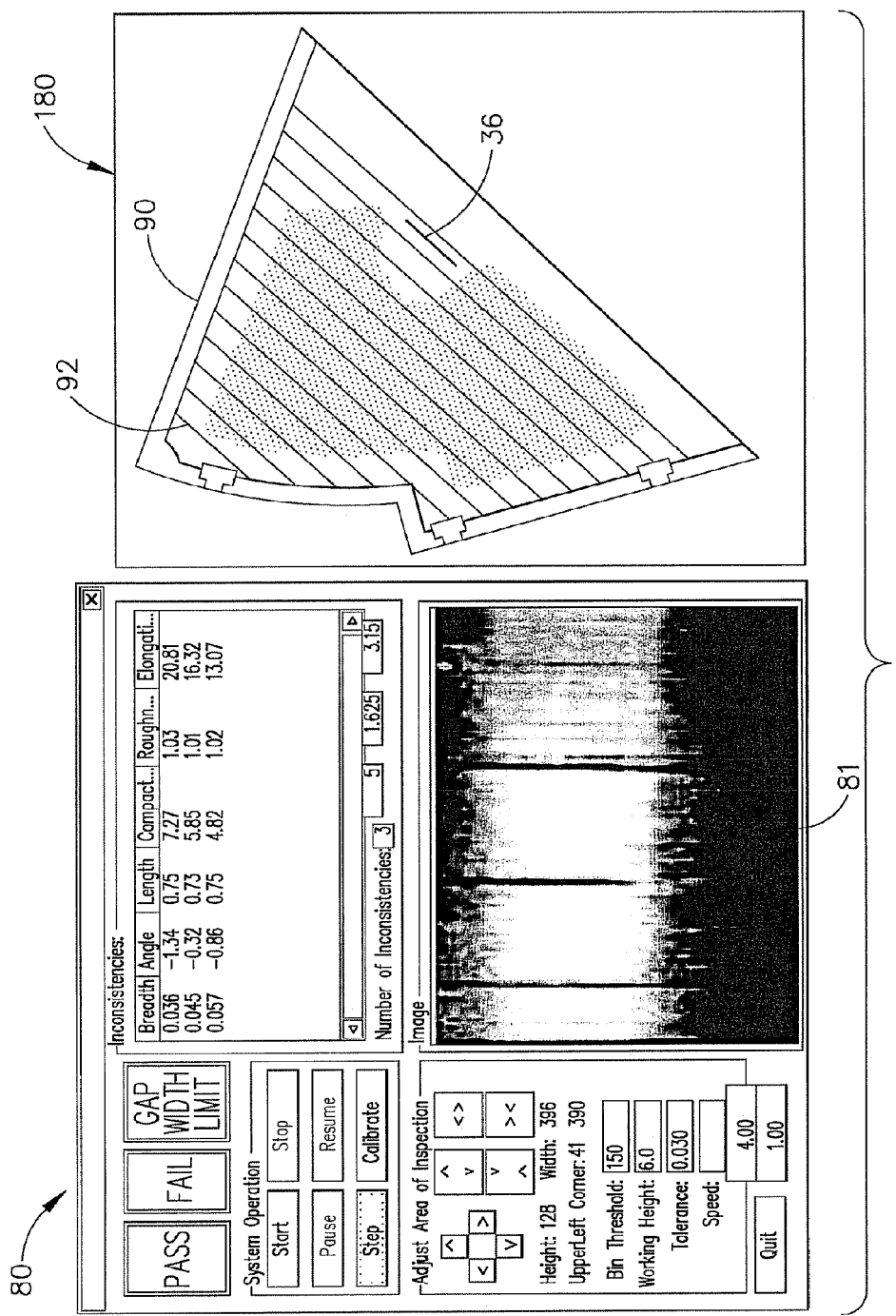
FIG. 14 is a view of two computer displays simultaneously displaying the computer display shown in FIG. 10 and the part model and course grid overlay shown in FIG. 13 according to one embodiment of the present disclosure.

FIG. 14 illustrates another embodiment in which two computer displays are employed for displaying and tracking the various inconsistency data for the imported model 90. As shown, one monitor displays the computer display 80 (previously described above in reference to FIG. 10) while the other monitor simultaneously displays a computer display 180 of the part model 90 and course grid overlay 92. The computer displays 80 and 180 can be continuously updated to show positioning and locations of inconsistencies as they are detected through the vision system interface, described above.

Figure 15:
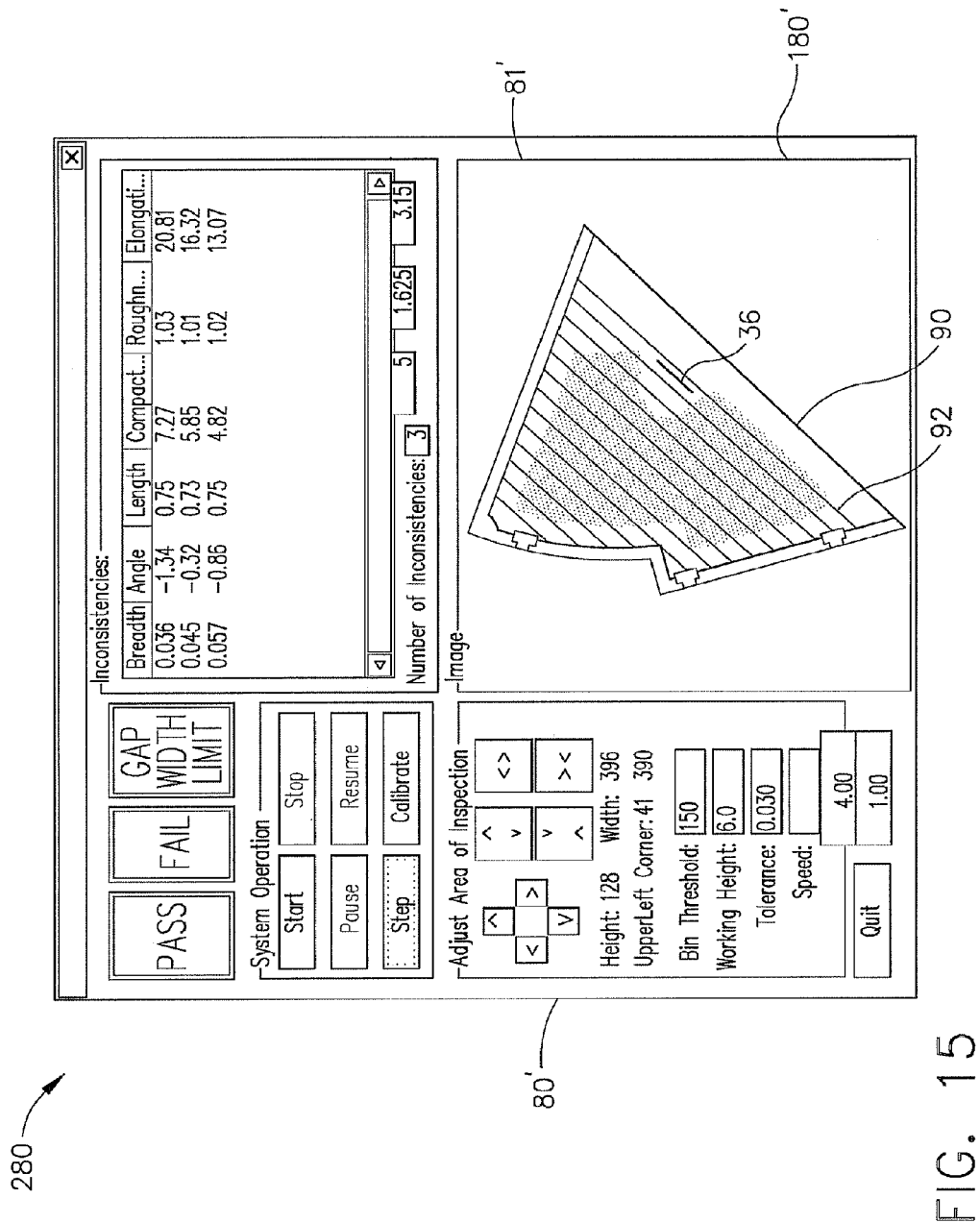
FIG. 15 is a view of a computer display according to one embodiment of the present disclosure.

FIG. 15 illustrates another embodiment 280 in which the display 180' of the part model 90 and course grid overlay 92 are displayed within the window 81' of computer display 80'.

Figure 16:
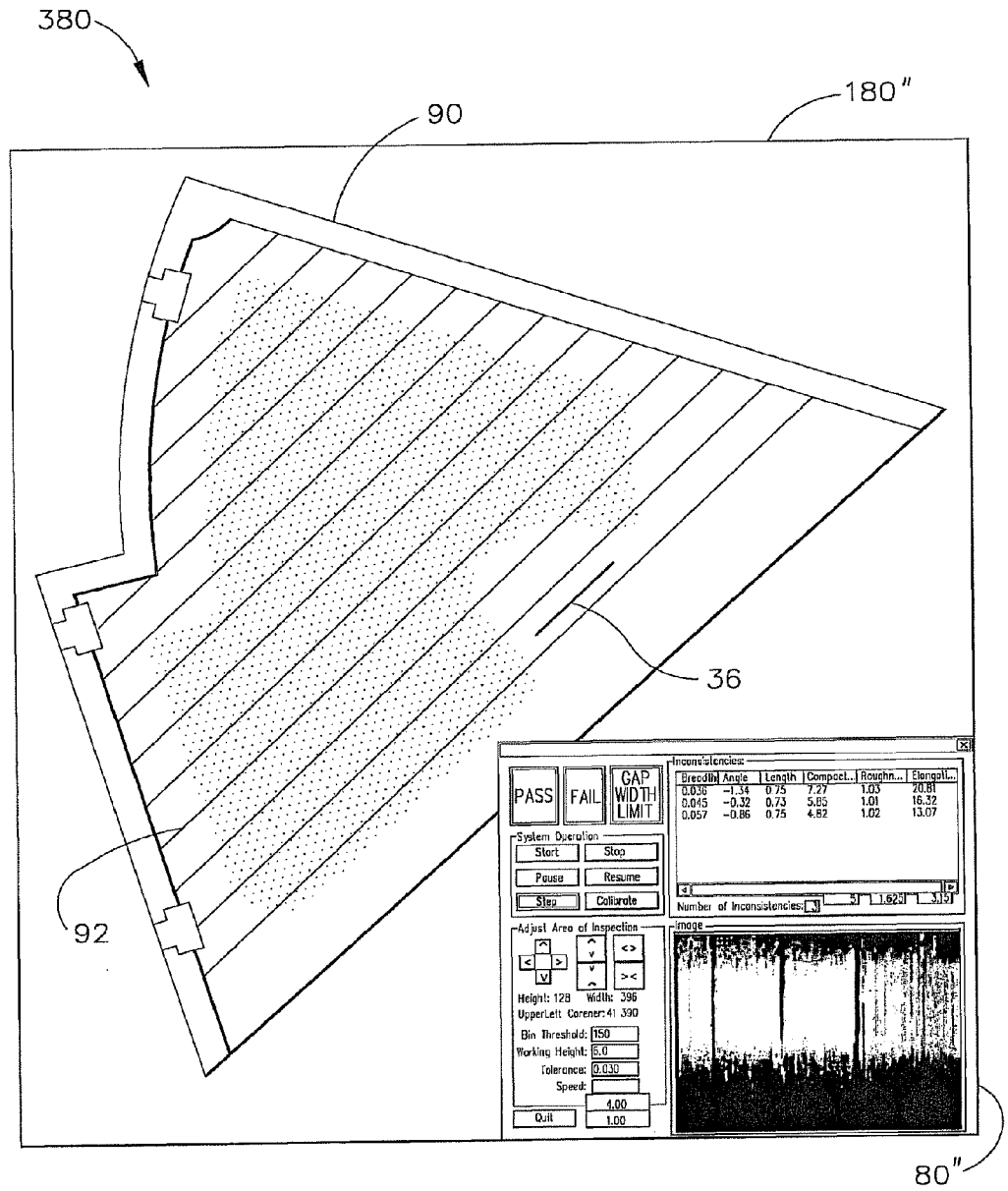
FIG. 16 is a view of a computer display according to one embodiment of the present disclosure.

FIG. 16 illustrates another embodiment 380 in which the display 80" is superimposed or positioned over a corner of the display 180" including the part model 90 and course grid overlay 92.

Accordingly, embodiments of the present disclosure provide in-process vision-based inspection systems and methods capable of accurately and efficiently determining various inconsistency characteristics such as total inconsistency count, total inconsistency width, inconsistency density-per-unit area, cumulative inconsistency width-per-unit area and/or inconsistency locations. Embodiments of the present disclosure allow composite structures to be fabricated more efficiently with fewer interruptions than conventional material placement systems which require manual inspections for and measuring of inconsistencies.

Embodiments of the present disclosure permit rapid detection and measurement of the cumulative inconsistency width-per-unit area, and tracking of the inconsistency density-per-unit area. Because this inconsistency information is relatively immediately available and manual measurement is not necessary, machine down-time can be significantly reduced resulting in reduced manufacturing costs and cycle times.

In addition, embodiments of the present disclosure allow for ready identification of those composite structures that exceed maximum allowable tolerances pertaining to density and cumulative width of inconsistencies. This allows the fabrication process to be halted when maximum allowable tolerances are exceeded, thereby saving time and materials which would otherwise be lost during continued fabrication of an unacceptable composite structure.

Further, when too many composite structures are being rejected, an operator can adjust the machines accordingly such that less material is wasted, less labor is expended, and less machine down time is incurred during the fabrication process. Therefore, a lower cost composite structure can be achieved on average.

Additionally, the various embodiments disclosed herein also enable improvements in the overall quality of the parts produced because inconsistency density and cumulative inconsistency width can be determined more uniformly and reliably with the various systems and methods of the present disclosure than with manual inspections.

While various embodiments have been described, those skilled in the art will recognize modifications or variations which might be made without departing from the inventive concept. The examples illustrate the present disclosure and are not intended to limit it. Therefore, the description and claims should be interpreted liberally with only such limitation as is necessary in view of the pertinent prior art.

What is claimed is:

1. A method for determining an inconsistency characteristic of a composite structure, the method comprising:
   determining a linear velocity of a material placement head unit along a course being laid by monitoring revolutions of a compaction roller of the material placement head unit;
   using the linear velocity to determine a linear distance from a first reference point along the course to an inconsistency of the composite structure;
   determining a lateral distance from a second reference point of the composite structure to the inconsistency;
   using the linear and lateral distances to establish a reference area; and
   summing inconsistencies within the reference area to produce a total inconsistency-count for the reference area.

2. The method of claim 1, further comprising dividing the total inconsistency count by the reference area to determine an inconsistency-density-per-unit area of the reference area.

3. The method of claim 1, wherein monitoring revolutions of a compaction roller comprises detecting, counting, and establishing frequency of transitions between contrasting portions of a code ring coupled for common rotation with the compaction roller.

4. A method for determining a location of an inconsistency of a composite structure under construction, the method comprising:
   determining a linear velocity of a compaction roller along a course being laid as the course is being laid by the compaction roller, said course forming a portion of said composite structure;
   selecting a first reference point along said course being laid;
   using the linear velocity to determine a linear distance from said first reference point along said course being laid to a detected inconsistency of the composite structure;
   selecting a second reference point;
   determining a lateral distance from said second reference point of the composite structure to said inconsistency; and
   using said linear and lateral distances to define a coordinate of said detected inconsistency.

5. The method of claim 4, wherein determining a linear velocity of a the compaction roller comprises monitoring revolutions of the compaction roller.

6. The method of claim 4, wherein determining a linear velocity of the compaction roller comprises determining an angular velocity of the compaction roller.

7. The method of claim 6, wherein determining said linear velocity further comprises multiplying said angular velocity by a circumference of said compaction roller.

8. The method of claim 6, wherein determining an angular velocity comprises determining a frequency of transitions between contrasting portions of a component operably associated with said compaction roller.

9. The method of claim 8, wherein determining said frequency of transition comprises determining a frequency of transitions between contrasting portions of a code ring adapted to rotate with the compaction roller.

10. The method of claim 4, wherein determining a lateral distance comprises:
    summing courses completed to produce a total completed course count; and
    multiplying a predetermined course width by said total completed course count.

* * * * *